(12) United States Patent
Sung et al.

(10) Patent No.: US 9,103,922 B2
(45) Date of Patent: *Aug. 11, 2015

(54) X-RAY IMAGING APPARATUS AND METHOD OF OPERATING THE SAME

(75) Inventors: Yong Hak Sung, Seongnam-Si (KR); Tae Gyun Kim, Seongnam-Si (KR)

(73) Assignee: VIEWORKS CO., LTD. (KR)

( * ) Notice: Subject to any disclaimer, the term of this patent is extended or adjusted under 35 U.S.C. 154(b) by 442 days.

This patent is subject to a terminal disclaimer.

(21) Appl. No.: 13/558,375

(22) Filed: Jul. 26, 2012

(65) Prior Publication Data

US 2013/0028381 A1 Jan. 31, 2013

(30) Foreign Application Priority Data

Jul. 29, 2011 (KR) .................. 10-2011-0076271

(51) Int. Cl.
 *G01N 23/04* (2006.01)
 *G01T 1/00* (2006.01)
 *G01T 1/20* (2006.01)
 *A61B 6/00* (2006.01)

(52) U.S. Cl.
 CPC ............. *G01T 1/2018* (2013.01); *A61B 6/4233* (2013.01); *A61B 6/542* (2013.01)

(58) Field of Classification Search
 CPC .... A61B 6/542; A61B 6/4233; G01T 1/2914; G01T 1/2018; H04N 5/32; H01G 1/30
 See application file for complete search history.

(56) References Cited

U.S. PATENT DOCUMENTS

| | | | | |
|---|---|---|---|---|
| 6,047,042 A * | 4/2000 | Khutoryansky et al. | ........ | 378/62 |
| 7,227,926 B2 * | 6/2007 | Kameshima et al. | ........ | 378/98.9 |
| 2002/0044211 A1 * | 4/2002 | Tujii et al. | ...................... | 348/302 |
| 2002/0186813 A1 * | 12/2002 | Tamura et al. | ................ | 378/98.8 |
| 2005/0047639 A1 * | 3/2005 | Hayashida | .................... | 382/132 |
| 2005/0110879 A1 * | 5/2005 | Izume et al. | ................ | 348/231.2 |
| 2007/0045552 A1 * | 3/2007 | Masazumi | ................ | 250/370.09 |
| 2007/0201617 A1 * | 8/2007 | Nakayama et al. | ............ | 378/108 |
| 2008/0169419 A1 * | 7/2008 | Petrick et al. | ............ | 250/370.09 |
| 2009/0201841 A1 * | 8/2009 | Tachikawa | .................... | 370/310 |
| 2009/0245465 A1 * | 10/2009 | Jung et al. | ...................... | 378/98.8 |
| 2011/0147596 A1 * | 6/2011 | Ishida et al. | .................. | 250/366 |
| 2011/0317809 A1 * | 12/2011 | Eguchi | ............................ | 378/62 |
| 2012/0075600 A1 * | 3/2012 | Sato et al. | ........................ | 355/18 |

(Continued)

FOREIGN PATENT DOCUMENTS

| | | |
|---|---|---|
| JP | 2007-111253 | 5/2007 |
| JP | 2009-236897 | 10/2009 |

*Primary Examiner* — Michael Logie
(74) *Attorney, Agent, or Firm* — Schmeiser, Olsen & Watts, LLP (57) ABSTRACT

An apparatus including a scintillator panel which absorbs X-rays radiated from an X-ray generator and converts the X-rays into visible light; an image detector including a plurality of pixels arranged in a matrix array and charging the plurality of pixels with electric charges proportional to intensity of the visible light converted by the scintillator panel; a gate driver which selects a line in the image detector and applies a drive signal to pixels in the selected line; an automatic exposure request signal generator which generates an automatic exposure request signal as a trigger signal informing of X-ray radiation through detection of X-rays radiated from the X-ray generator; and a controller which controls a time point of performing an exposure operation depending on a state of the drive signal applied to the pixels of the selected line in response to the automatic exposure request signal is disclosed.

9 Claims, 10 Drawing Sheets

(56) References Cited

U.S. PATENT DOCUMENTS

2012/0091353 A1* 4/2012 Enomoto ................. 250/370.08
2012/0106700 A1* 5/2012 Jung ............................... 378/62
2012/0119100 A1* 5/2012 Muraoka .................. 250/370.09
2012/0132810 A1* 5/2012 Uchiyama .................. 250/358.1
2012/0134474 A1* 5/2012 Duca et al. ....................... 378/96
2014/0348299 A1* 11/2014 Sung et al. ....................... 378/91

* cited by examiner

X-RAY IMAGING APPARATUS AND METHOD OF OPERATING THE SAME

BACKGROUND

1. Technical Field

The present invention relates to an X-ray imaging apparatus and an operating method thereof. More particularly, the present invention relates to an X-ray imaging apparatus capable of photographing an X-ray image without loss of X-ray radiation even without an additional device for sharing a synchronizing signal with an X-ray generator, and a method of operating the same.

2. Description of the Related Art

Generally, an X-ray diagnosis system is constituted by an X-ray generator which generates X-rays and irradiates an object with the X-rays, and an X-ray imaging apparatus for photographing an X-ray image of the object.

In such an X-ray diagnosis system, the X-ray imaging apparatus sequentially perform a flush operation for eliminating dark current from an image sensor in each line, an exposure operation for absorbing X-rays radiated from the X-ray generator, and a read-out operation for allowing the X-ray imaging apparatus to read charges generated by X-ray radiation and to output image data.

Here, in response to an exposure request signal from the X-ray generator during a flush operation, the X-ray imaging apparatus completes the flush operation throughout an overall area and performs an exposure operation by sending an exposure preparation completion signal, which informs the X-ray generator of completion of preparation for exposure operation.

Such a trigger manner by handshaking a state signal between the X-ray generator and the X-ray imaging apparatus is referred to as an active line trigger manner.

For an active line trigger type X-ray generator, the X-ray imaging apparatus can complete the flush operation for a duration between a time point of receiving an exposure request signal and a time point of sending an exposure preparation completion signal, thereby providing high quality image data.

However, when using a passive line trigger type X-ray generator which radiates X-rays by sending only an exposure request signal to the X-ray imaging apparatus, or a non-line trigger type X-ray generator which radiates X-rays without sending an exposure request signal to the X-ray imaging apparatus, loss of X-rays occurs due to time consumption upon changeover from the flush operation of the X-ray imaging apparatus to the exposure operation thereof, thereby making it difficult to obtain high quality image data.

Further, when the X-ray imaging apparatus performs the exposure operation without completing the flush operation for lines in some areas in order to reduce loss of X-rays, there is a problem of deterioration in image data in each line.

Meanwhile, the X-ray imaging apparatus generally adopts a progressive flush method, in which the flush operation is continuously carried out from the first line to the last line at a gate stage in an image detector.

However, since the progressive flush method requires a relatively long time until the flush operation is completed, large amounts of X-rays can be lost when the progressive flush operation is applied to the passive line trigger type or the non-line trigger type.

BRIEF SUMMARY

The present invention has been conceived to solve such problems in the related art and an aspect of the present invention is to provide an X-ray imaging apparatus capable of generating a trigger signal through detection of radiated X-rays.

Another aspect of the present invention is to provide a method of operating an X-ray imaging apparatus, which may reduce time for a flush operation in an interface condition where X-rays are radiated in a non-synchronized manner and may minimize loss of radiated X-rays, thereby providing high quality image data.

In accordance with an aspect of the present invention, an X-ray imaging apparatus includes: a scintillator panel which absorbs X-rays radiated from an X-ray generator and converts the X-rays into visible light; an image detector including a plurality of pixels arranged in a matrix array and charging the plurality of pixels with electric charges proportional to intensity of the visible light converted by the scintillator panel; a gate driver which selects a line in the image detector and applies a drive signal to pixels in the selected line; and a controller which controls a time point of performing an exposure operation depending on a state of the drive signal applied to the pixels of the selected line in response to an exposure request signal informing of X-ray radiation from the X-ray generator.

The controller may complete preparation for the exposure operation after application of the drive signal is completed, when the drive signal applied to the pixels of the selected line is in an active state at a time point of receiving the exposure request signal.

The apparatus may further include a signal processor which processes the exposure request signal received from the X-ray generator; and a read-out unit which reads an amount of electric charges in the pixels of the selected line.

In accordance with another aspect of the present invention, an X-ray imaging apparatus includes: a scintillator panel which absorbs X-rays radiated from an X-ray generator and converts the X-rays into visible light; an image detector including a plurality of pixels arranged in a matrix array and charging the plurality of pixels with electric charges proportional to intensity of the visible light converted by the scintillator panel; a gate driver which selects a line in the image detector and applies a drive signal to pixels in the selected line; an automatic exposure request signal generator which generates an automatic exposure request signal as a trigger signal informing of X-ray radiation through detection of X-rays radiated from the X-ray generator; and a controller which controls a time point of performing an exposure operation depending on a state of the drive signal applied to the pixels of the selected line in response to the automatic exposure request signal.

The controller may complete preparation for the exposure operation after application of the drive signal is completed, when the drive signal applied to the pixels of the selected line is in an active state at a time point of receiving the automatic exposure request signal.

The automatic exposure request signal generator may include a light converter which converts X-rays radiated from the X-ray generator into visible light; a light detector which detects the visible light converted by the light converter and converts the visible light into an electric signal; an amplifier which amplifies the electric signal converted by the light detector; and a trigger conversion circuit which converts the electric signal amplified by the amplifier into a digital signal to generate the automatic exposure request signal.

The light converter may be a scintillator.

The automatic exposure request signal generator may include a light detector which detects the visible light converted by the scintillator panel and converts the visible light into an electric signal; an amplifier which amplifies the electric signal converted by the light detector; and a trigger conversion circuit which converts the electric signal amplified by the amplifier into a digital signal to generate the automatic exposure request signal.

The automatic exposure request signal generator may include an X-ray detector which detects X-rays radiated from the X-ray generator and converts the X-rays into an electric signal; an amplifier which amplifies the electric signal converted by the X-ray detector; and a trigger conversion circuit which converts the electric signal amplified by the amplifier into a digital signal to generate the automatic exposure request signal.

The automatic exposure request signal generator may be placed on each of lower surfaces of the scintillator panel and the image detector with respect to a direction of radiated X-rays.

The automatic exposure request signal generator may be placed at a location corresponding to a center or a corner of the image detector.

The X-ray imaging apparatus may further include a read-out unit which reads a value of charges in the pixels of the selected line.

In accordance with a further aspect of the present invention, a method of operating an X-ray imaging apparatus includes receiving, by a controller, a trigger signal informing of X-ray radiation; determining, by the controller, whether a drive signal is applied to pixels of a selected line in an image detector including a plurality of pixels arranged in a matrix array to perform a flush operation, upon receiving the trigger signal; and performing, by the controller, an exposure operation after completion of the flush operation.

The trigger signal may be an exposure request signal received from an X-ray generator.

The method may further include detecting, by an automatic exposure request signal generator, X-rays radiated from an X-ray generator to generate the trigger signal before receiving the trigger signal.

Generation of the trigger signal may include converting X-rays radiated from the X-ray generator into visible light; detecting and converting the visible light into an electric signal; amplifying the electric signal; and converting the amplified electric signal into a digital signal to generate the trigger signal.

The flush operation may be performed in a multiple-gate flush manner by dividing all lines in the image detector into a plurality of unit gate blocks and simultaneously applying the drive signal to each of the unit gate blocks.

The flush operation may be performed in a multiple-channel-gate flush manner by dividing all lines in the image detector into a plurality of unit gate blocks and simultaneously applying the drive signal to each of the unit gate blocks such that the drive signal is simultaneously applied to a plurality of lines in the unit gate blocks.

In accordance with a further aspect of the present invention, a method of operating an X-ray imaging apparatus includes dividing all lines in an image detector including a plurality of pixels arranged in a matrix array into a plurality of unit gate blocks; and performing a flush operation in a multiple-gate flush manner by simultaneously applying a drive signal to each of the unit gate blocks.

The flush operation may be performed in a multiple-channel-gate flush manner by simultaneously applying the drive signal to each of the unit gate blocks such that the drive signal is simultaneously applied to a plurality of lines in the unit gate blocks.

According to the present invention, when a trigger signal informing of X-ray radiation is received during a flush operation in the X-ray imaging apparatus, exposure operation is carried out after finishing the flush operation for a selected line, thereby preventing deterioration of image data in each line to provide image date of good quality.

At this time, according to the present invention, a flush operation is performed in a multiple-gate or multiple-channel-gate manner to shorten time for the flush operation, thereby minimizing loss of X-rays in an interface condition wherein X-rays are radiated in a non-synchronization manner.

In addition, according to the present invention, X-rays radiated are detected to generate an automatic exposure request signal functioning as a trigger signal, thereby preventing deterioration of image data in each line and providing high quality image data even in the case of adopting a non-line trigger type X-ray generator.

Further, according to the present invention, since a module for generating an automatic exposure request signal is placed inside the X-ray imaging apparatus, the X-ray imaging apparatus may be realized by a single system without separate interface equipment, thereby improving user convenience while enabling X-ray detection without any restriction on an X-ray radiation range in a practical site.

Furthermore, according to the present invention, in generation of an automatic exposure request signal, the light converter for converting X-rays into visible light is attached to the front side of the light detector, thereby improving efficiency in detection of X-rays having passed through the scintillator panel and the image detector while blocking undesired light.

BRIEF DESCRIPTION OF THE DRAWINGS

The above and other aspects, features and advantages of the present invention will become apparent from the following description of embodiments given in conjunction with the accompanying drawings, in which.

DETAILED DESCRIPTION

Exemplary embodiments of the present invention will now be described in detail with reference to the accompanying drawings. It should be noted that the drawings are not to precise scale and may be exaggerated in thickness of lines or size of components for descriptive convenience and clarity. Furthermore, the terms used herein are defined by taking functions of the present invention into account and can be changed according to user or operator's custom or intention. Therefore, definition of the terms should be made according to the overall disclosure set forth herein.

Figure 1:
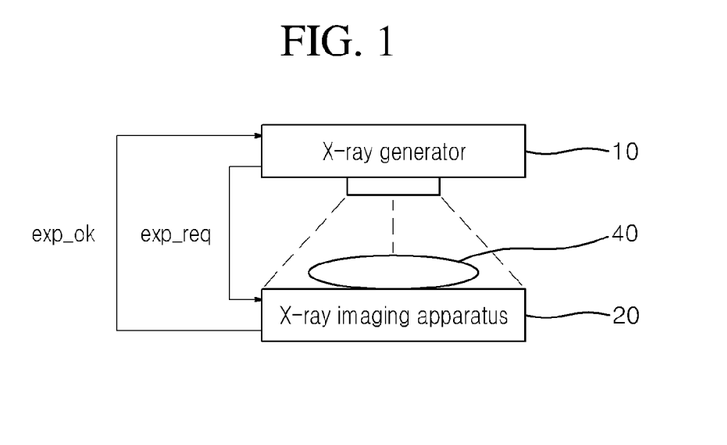
FIG. 1 shows X-ray radiation from an active line trigger type X-ray generator to an X-ray imaging apparatus.
Figure 2:
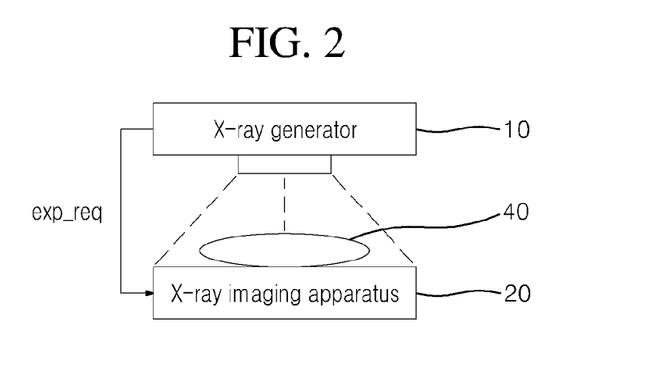
FIG. 2 shows X-ray radiation from a passive line trigger type X-ray generator to an X-ray imaging apparatus.

FIG. 1 shows X-ray radiation from an active line trigger type X-ray generator to an X-ray imaging apparatus and FIG. 2 shows X-ray radiation from a passive line trigger type X-ray generator to an X-ray imaging apparatus.

Figure 3:
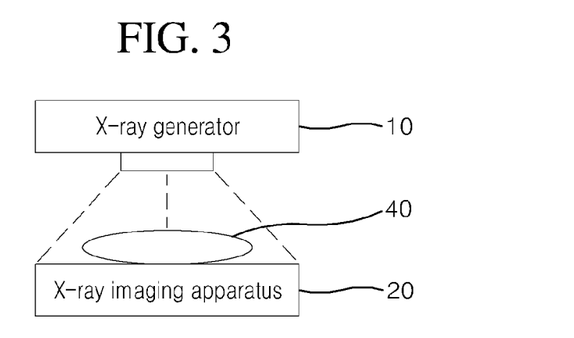
FIG. 3 shows X-ray radiation from an X-ray generator, which does not support a line trigger type operation, to an X-ray imaging apparatus.

FIG. 3 shows X-ray radiation from an X-ray generator, which does not support a line trigger type operation, to an X-ray imaging apparatus.

An X-ray generator 10 generates X-rays to irradiate an object 40 with the X-rays. The X-ray generator 10 may be provided with a switch (not shown) to radiate X-rays in response to an operation signal input by a user, and includes various components used for X-ray generation.

Referring to FIG. 1, when receiving an operation signal input by a user, an active line trigger type X-ray generator 10 sends an exposure request signal (exp_req) to an X-ray imaging apparatus 20 to confirm preparation for X-ray detection, and irradiates an object 40 with X-rays upon receiving an exposure permission signal (exp_ok) from the X-ray imaging apparatus 20.

Meanwhile, referring to FIG. 2, upon receiving an operation signal input by a user, a passive line trigger type X-ray generator 10 sends an exposure request signal (exp_req) to the X-ray imaging apparatus 20 to confirm preparation for X-ray detection, and irradiates the object 40 with X-rays.

Further, referring to FIG. 3, upon receiving an operation signal input by a user, a non-line trigger type X-ray generator 10, which does not support a line trigger type operation, irradiates the object 40 with X-rays without sending an exposure request signal (exp_req) to the X-ray imaging apparatus 20.

Figure 4:
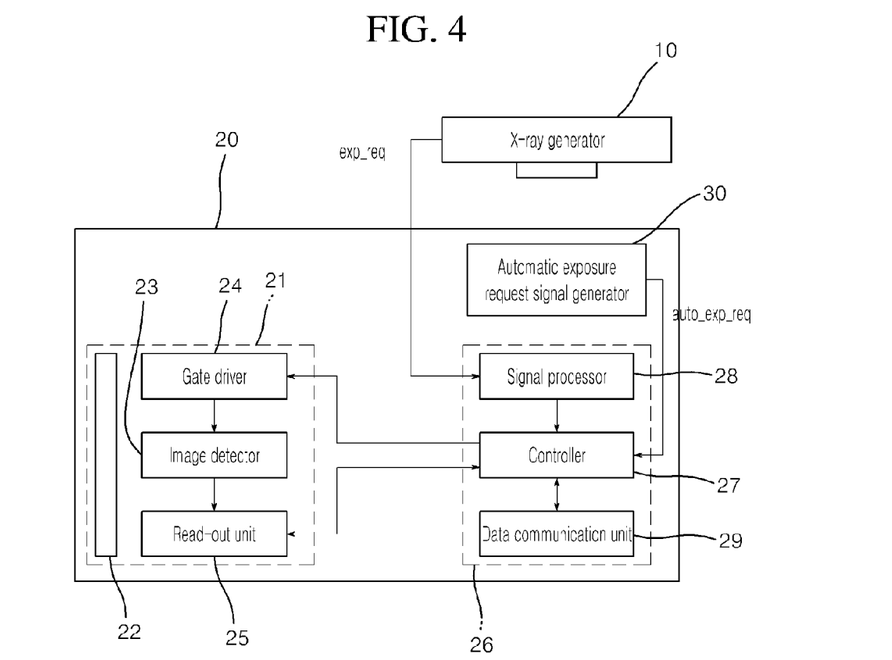
FIG. 4 is a block diagram of an X-ray imaging apparatus in accordance with one embodiment of the present invention.
Figure 5:
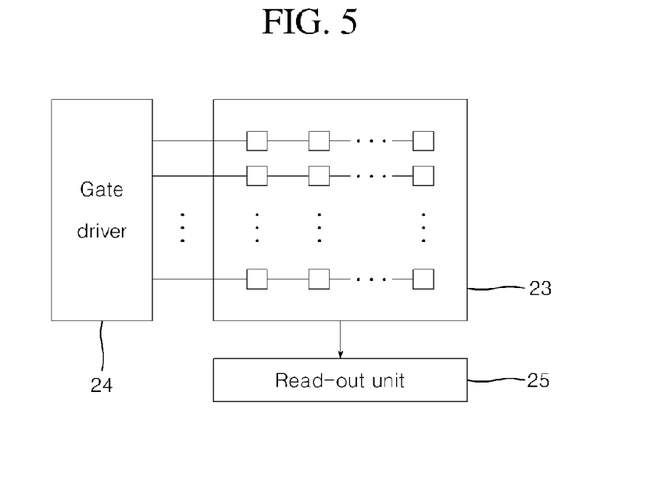
FIG. 5 is a view of a configuration for performing gate selection and read-out in the X-ray imaging apparatus in accordance with the embodiment of the present invention.

FIG. 4 is a block diagram of an X-ray imaging apparatus in accordance with one embodiment of the present invention, and FIG. 5 is a view of a configuration for performing gate selection and read-out in the X-ray imaging apparatus in accordance with the embodiment of the present invention.

An X-ray imaging apparatus 20 according to this embodiment detects X-rays having passed through an object 40 to obtain an X-ray image of the object 40.

Referring to FIGS. 4 and 5, the X-ray imaging apparatus 20 according to this embodiment includes an image sensor unit 21, a printed circuit board 26, and an automatic exposure request signal generator 30.

The image sensor unit 21 includes a scintillator panel 22, an image detector 23, a gate driver 24, and a read-out unit 25.

The scintillator panel 22 converts X-rays radiated from the X-ray generator 10 into visible light.

The image detector 23 detects the visible light converted by the scintillator panel 22. The image detector 23 includes a plurality of pixels arranged in a matrix array, as shown in FIG. 5, and supplies charges to each of pixels in proportion to the intensity of visible light detected thereby.

The gate driver 24 sequentially selects lines in the image detector 23 to apply a drive signal thereto and is controlled by a controller 27.

When the drive signal is applied to a certain line by the gate driver 24, the read-out unit 25 described below may read a value of charges in the pixels of the selected line.

Here, the drive signal applied by the gate driver 24 may be a voltage signal which turns on a thin film transistor (TFT) connected to each of the pixels in the line.

When the drive signal is applied to a certain line of the image detector 23, the read-out unit 25 reads the value of charges in each of the pixels in the line.

At this time, upon a flush operation, the read-out unit 25 may discard the value of charges in each of the pixels instead of reading the value of charges, thereby eliminating dark current accumulated in each of the pixels in the image detector 23.

On the contrary, upon a read-out operation, the read-out unit 25 may obtain analogue data in the form of voltage by reading the value of charges in each of the pixels, convert the analogue data into digital data, and send the digital data to the controller 27.

Upon receiving the digital data from the read-out unit 25, the controller 27 combines the digital data for each line and sends the combined digital data to a PC through a data communication unit 29.

Figure 6:
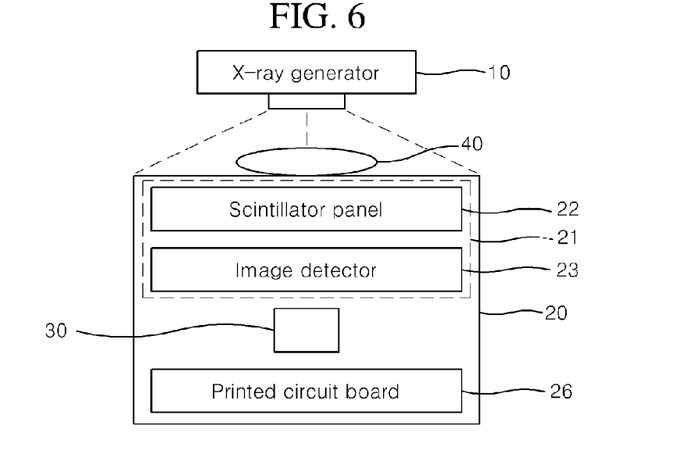
FIG. 6 is a stratum diagram of the X-ray imaging apparatus in accordance with the embodiment of the present invention.
Figure 7:
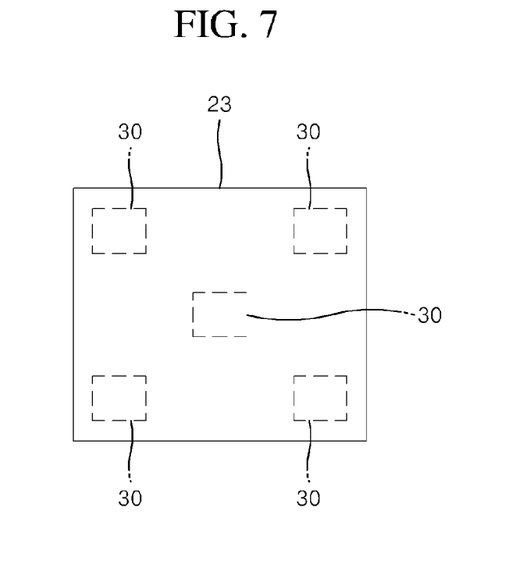
FIG. 7 is a top view of the X-ray imaging apparatus in accordance with the embodiment of the present invention, showing installation positions of an automatic exposure request signal generators therein.
Figure 8:
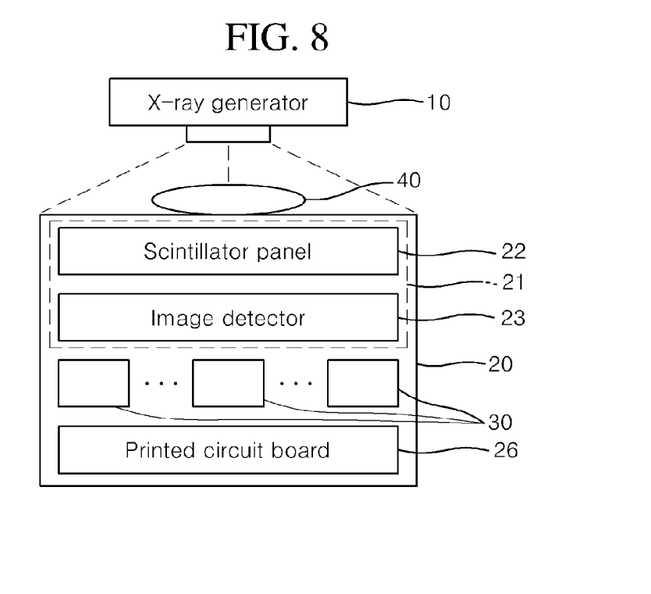
FIG. 8 is a side view of the X-ray imaging apparatus in accordance with the embodiment of the present invention, showing the installation positions of the automatic exposure request signal generators therein.

FIG. 6 is a stratum diagram of the X-ray imaging apparatus in accordance with the embodiment; FIG. 7 is a top view of the X-ray imaging apparatus in accordance with the embodiment, showing installation positions of an automatic exposure request signal generators therein; and FIG. 8 is a side view of the X-ray imaging apparatus in accordance with the embodiment, showing the installation positions of the automatic exposure request signal generators therein.

The automatic exposure request signal generator 30 generates an automatic exposure request signal (auto_exp_req) as a trigger signal informing of X-ray radiation by detecting X-rays radiated from the X-ray generator 10, and sends the automatic exposure request signal to the controller 27.

Such an automatic exposure request signal generator 30 may be disposed within the X-ray imaging apparatus 20. For example, as shown in FIG. 6, the automatic exposure request signal generator 30 may be placed on a lower surface of the image sensor unit 21, which includes the X-ray scintillator panel 22 and the image detector 23, with respect to radiated X-rays.

Alternatively, the automatic exposure request signal generator 30 may be placed on the printed circuit board 26, on which a signal processor 28, the controller 27 and the data communication unit 29 are placed.

As a result, the automatic exposure request signal generator 30 may generate the automatic exposure request signal (auto_exp_req) by detecting X-rays having passed through the scintillator panel 22 and the image detector 23.

In this way, with the automatic exposure request signal generator 30, the X-ray imaging apparatus 20 may be realized by a single system without separate interface equipment, thereby improving user convenience while enabling X-ray detection without any restriction on an X-ray radiation range.

Further, as shown in FIGS. 7 and 8, the X-ray imaging apparatus 20 may include a plurality of automatic exposure request signal generators 30 disposed at locations corresponding to the center and corners of the image sensor unit 21 which includes the scintillator panel 22 and the image detector 23.

When the plurality of automatic exposure request signal generators 30 are disposed at several locations in the X-ray imaging apparatus 20, an automatic exposure request signal (auto_exp_req) may be formed through the automatic exposure request signal generators 30, which are disposed at the corners of the image sensor unit and thus are not affected by the object 40, in the case where the amount of X-rays transmission is reduced at the center of the image sensor by the object 40.

In this embodiment, the automatic exposure request signal generators 30 are illustrated as being disposed at the center and the corners of the image detector 23. However, it should be understood that the placement positions and number of the automatic exposure request signal generators 30 may be selected in various ways according to the designer's intention and purpose.

Figure 9:
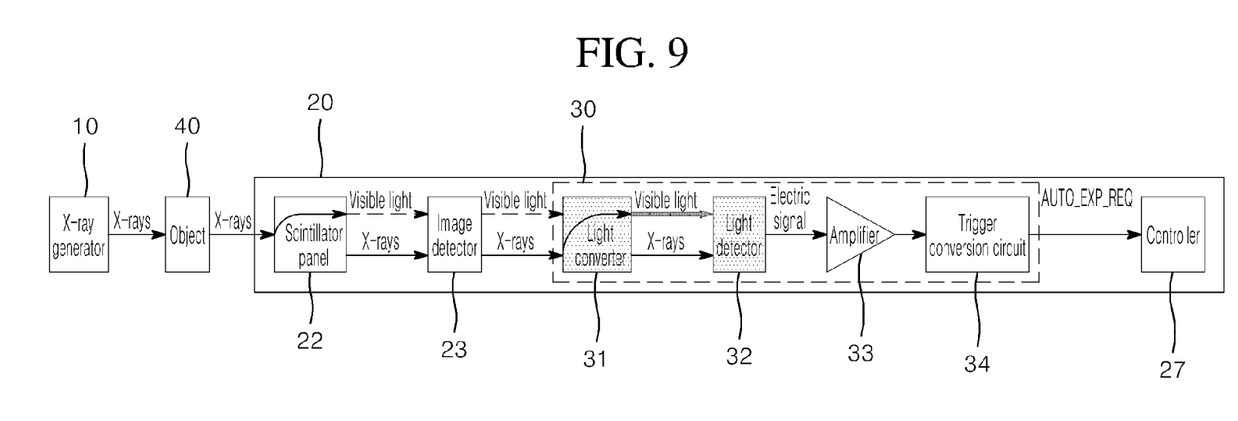
FIG. 9 is a view of a process of generating an automatic exposure request signal in the X-ray imaging apparatus in accordance with the embodiment of the present invention.

FIG. 9 is a view of a process of generating an automatic exposure request signal in the X-ray imaging apparatus in accordance with the embodiment of the present invention.

Referring to FIG. 9, the automatic exposure request signal generator 30 may include a light converter 31, a light detector 32, an amplifier 33, and a trigger conversion circuit 34.

The light converter 31 is attached to a front side of the light detector 32 and converts X-rays radiated from the X-ray generator 10 into visible light. The light converter 31 may include a scintillator or other materials capable of converting X-rays into visible light.

The light detector 32 detects the visible light converted by the light converter 31 and converts the detected visible light into an electric signal. The light detector 32 may be realized by a photo diode or other devices capable of detecting visible light.

The amplifier 33 amplifies the electric signal converted by the light detector 32 and sends the amplified electric signal to the trigger conversion circuit 34. Then, the trigger conversion circuit 34 converts the electric signal amplified by the amplifier 33 into a digital signal to generate an automatic exposure request signal (auto_exp_req) functioning as a trigger signal informing of X-ray radiation, and sends the automatic exposure request signal to the controller 27.

Figure 10:
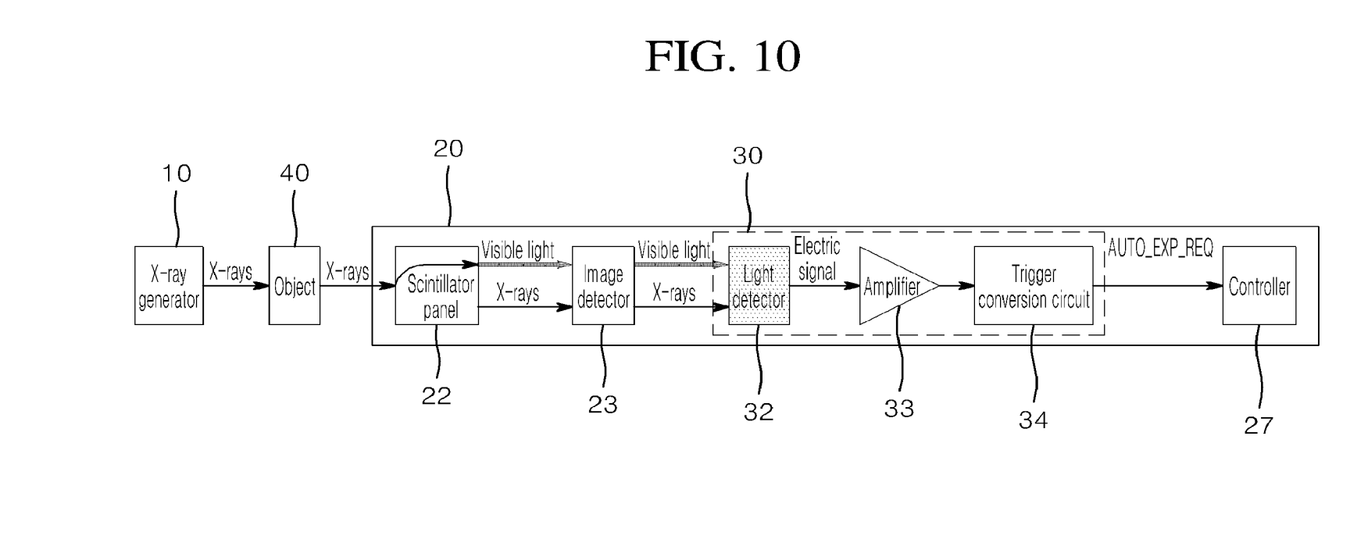
FIG. 10 is a view of a process of generating an automatic exposure request signal in an X-ray imaging apparatus in accordance with another embodiment of the present invention.

FIG. 10 is a view of a process of generating an automatic exposure request signal in an X-ray imaging apparatus in accordance with another embodiment.

Referring to FIG. 10, the automatic exposure request signal generator 30 according to this embodiment need not include the light converter 31.

Specifically, the automatic exposure request signal generator 30 may generate an automatic exposure request signal (auto_exp_req) by directly detecting visible light emitted from the scintillator panel 22, which absorbs X-rays from the X-ray generator 10, through the light detector 32.

Figure 11:
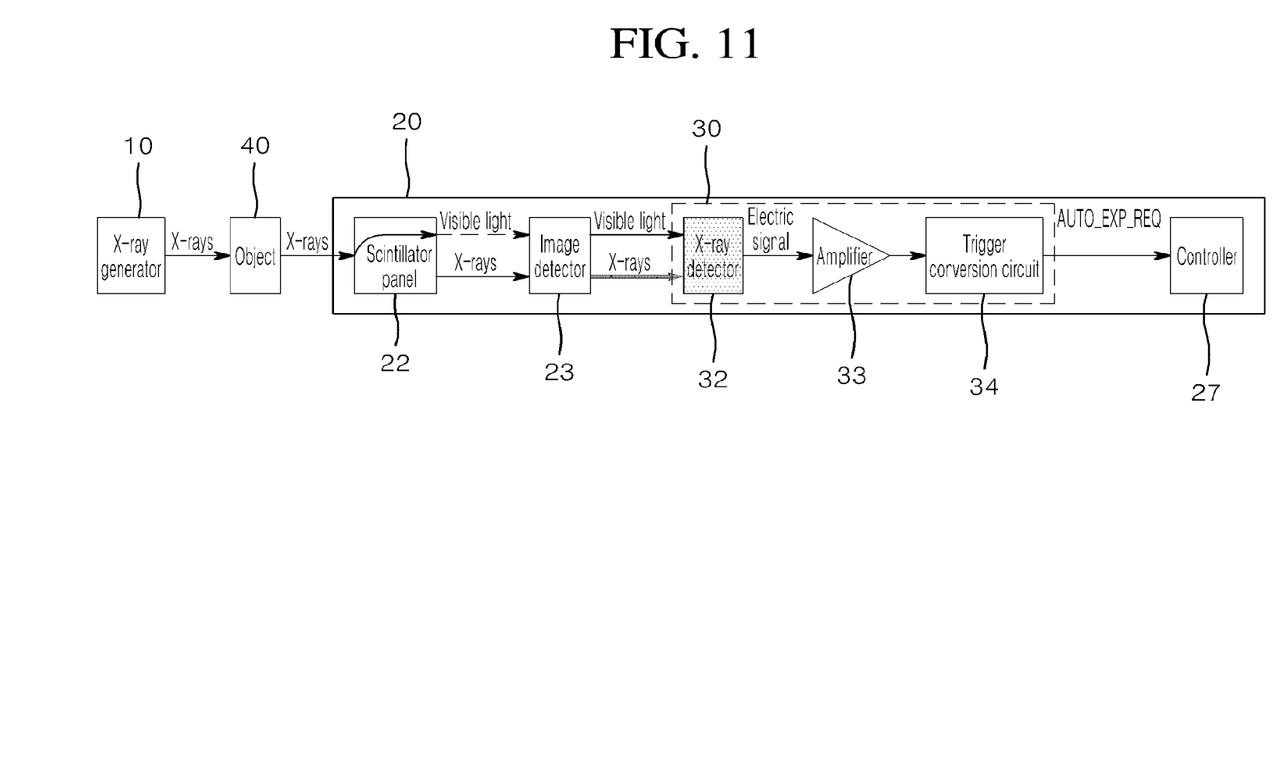
FIG. 11 is a view of a process of generating an automatic exposure request signal in an X-ray imaging apparatus in accordance with a further embodiment of the present invention.

FIG. 11 is a view of a process of generating an automatic exposure request signal in an X-ray imaging apparatus in accordance with a further embodiment.

Referring to FIG. 11, an automatic exposure request signal generator 30 according to this embodiment may include an X-ray detector 35 capable of directly detecting X-rays instead of the light converter 31 and the light detector 32.

Specifically, the automatic exposure request signal generator 30 may generate an automatic exposure request signal (auto_exp_req) by detecting X-rays having passed through the scintillator panel 22 and the image detector 23 using the X-ray detector 35.

The X-ray detector 35 includes various devices capable of detecting X-rays.

According to the present invention, the X-ray imaging apparatus may generate an automatic exposure request signal (auto_exp_req) functioning as a trigger signal by detecting radiated X-rays, thereby providing a high quality X-ray image in the case of using the X-ray generator 10 which does not support the line trigger type operation.

Meanwhile, the printed circuit board 26 is provided with an electronic circuit module, and includes the signal processor 28, the controller 27 and the data communication unit 29.

The signal processor 28 processes the exposure request signal (exp_req) received from the X-ray generator 10 according to a voltage level and sends the processed signal to the controller 27.

The controller 27 controls the overall operation of the X-ray imaging apparatus to obtain X-ray images using X-rays emitted from the X-ray generator 10 by controlling the gate driver 24 and the read-out unit 25.

In other words, the controller 27 controls overall procedures for flush operation, exposure operation and read-out operation of the X-ray imaging apparatus 20.

Upon receiving the trigger signal informing of X-ray radiation, the controller 27 controls the X-ray imaging apparatus to perform an exposure operation after completion of a flush operation with respect to a certain line, which is selected by the gate driver 24.

When the passive line trigger type X-ray generator 10 is used, the trigger signal received by the controller 27 may be an exposure request signal (exp_req) that is received from the X-ray generator 10 through the signal processor 28.

Further, when the X-ray generator 10 not supporting a line trigger type operation is used, the trigger signal received by the controller 27 may be an automatic exposure request signal (auto_exp_req), which is generated by detecting radiated X-rays.

Finally, the data communication unit 29 sends image data, which is obtained by combination of digital data for each line through read-out operation in the controller 27, to a PC.

Figure 12:
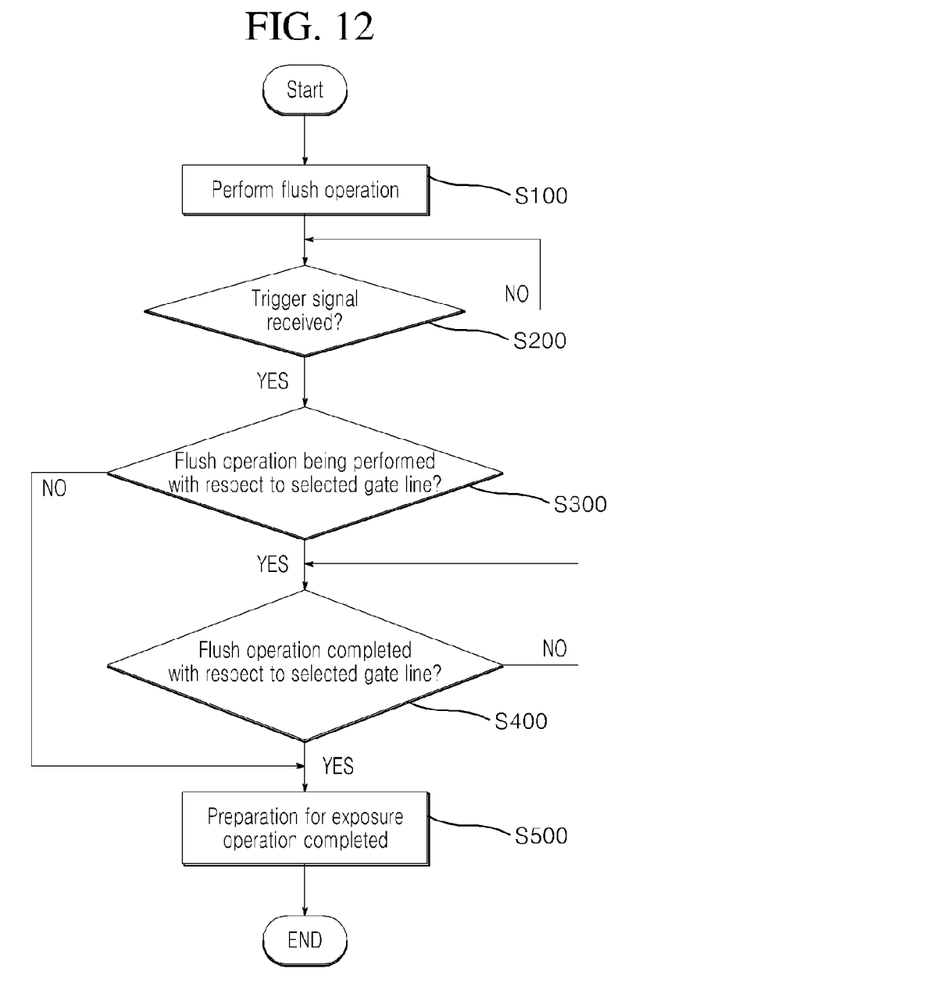
FIG. 12 is a flowchart of a method of operating an X-ray imaging apparatus in accordance with one embodiment of the present invention.

FIG. 12 is a flowchart of a method of operating an X-ray imaging apparatus in accordance with one embodiment of the present invention.

Figure 13:
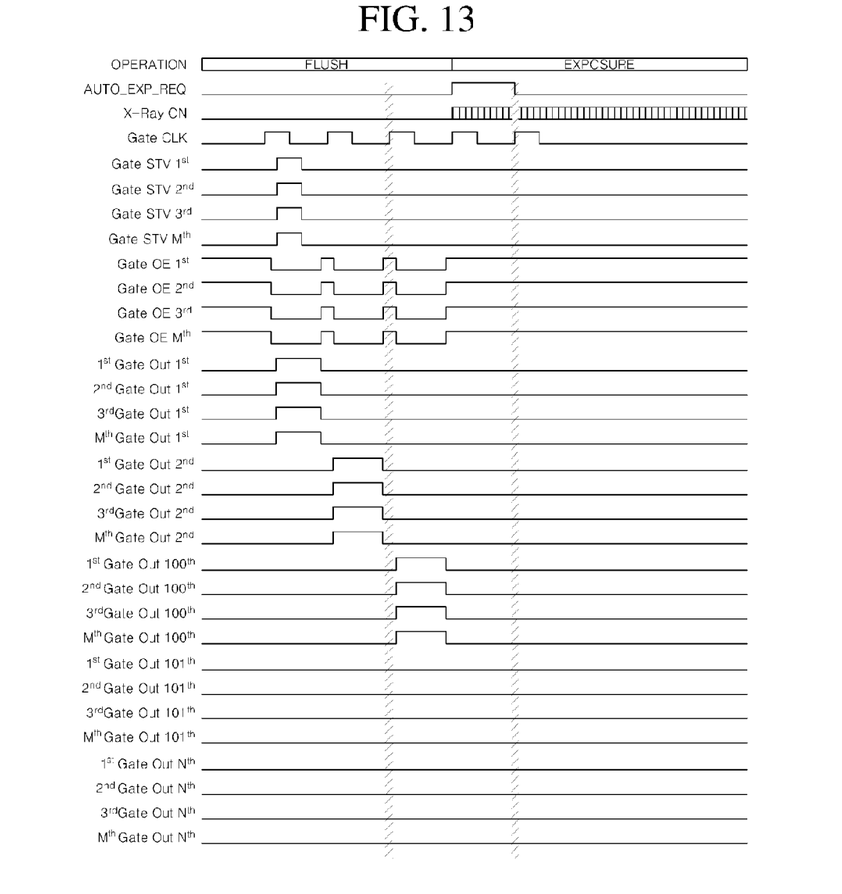
FIG. 13 is a timing diagram illustrating a flush operation in a multiple-gate flush manner in the method of operating an X-ray imaging apparatus in accordance with the embodiment of the present invention.
Figure 14:
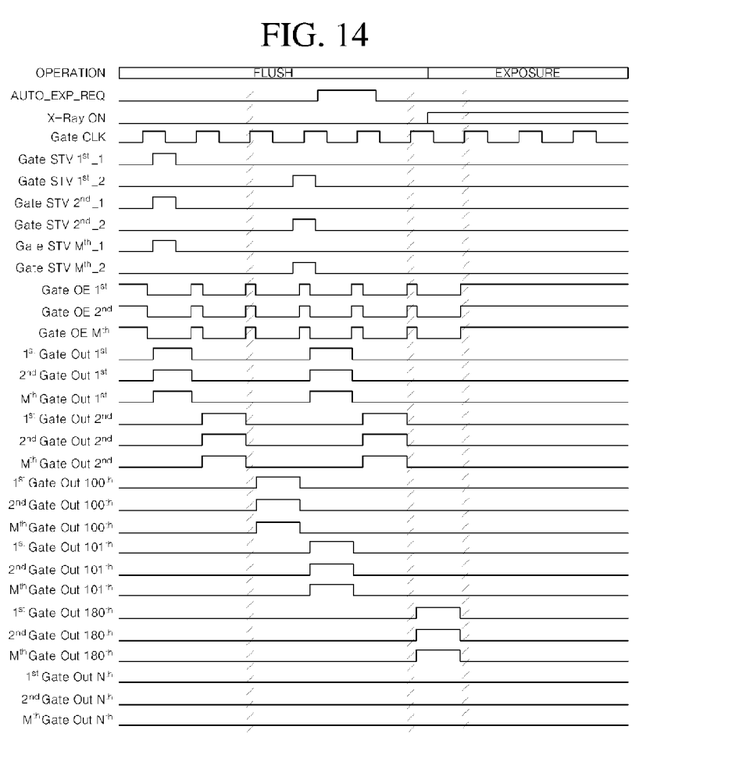
FIG. 14 is a timing diagram illustrating a flush operation in a multiple-channel-gate flush manner in the method of operating an X-ray imaging apparatus in accordance with the embodiment of the present invention.

FIG. 13 is a timing diagram illustrating a flush operation in a multiple-gate flush manner in the method of operating an X-ray imaging apparatus in accordance with the embodiment; and FIG. 14 is a timing diagram illustrating a flush operation in a multiple-channel-gate flush manner in the method of operating an X-ray imaging apparatus in accordance with the embodiment.

In FIGS. 13 and 14, Gate CLK means a gate clock signal determining an application timing of a drive signal, Gate STV means a scan start pulse signal, Gate OE means a gate output control signal, and Gate Out means a drive signal applied to a line.

The numerals following each of the scan start pulse signal (Gate STV) and the gate output control signal (Gate OE) mean first to $M^{th}$ unit gate blocks.

Further, the numerals in front of the drive signal (Gate Out) mean first to $M^{th}$ unit gate blocks, and the numerals following the drive signal mean first to $N^{th}$ lines in each of the unit gate blocks.

Next, operation of the X-ray imaging apparatus according to the present invention will be described in detail with reference to FIG. 12 to FIG. 14.

In FIG. 12, the controller 27 controls the gate driver 24 and the read-out unit 25 to sequentially select certain lines of the image detector 23 and allows a flush operation to be performed to flush dark current accumulated in the corresponding line (S100).

The controller 27 may allow the flush operation to be performed in a multiple-gate flush manner or in a multiple-channel-gate flush manner.

In the multiple-gate flush manner, the image detector 23 is divided into M unit gate blocks, and the respective unit gate blocks are subjected to a progressive flush operation at the same time.

Specifically, in the multiple-gate flush manner, the flush operation is performed in such a way that, with N lines of the image detector 23 defined as unit gate blocks and a gate stage of the image detector 23 divided into the M unit gate blocks, a drive signal is simultaneously applied to a sequentially selected line in each of the unit gate blocks.

Referring to FIG. 13, it can be seen that a drive signal is simultaneously applied to a sequentially selected line from the first line to the $N^{th}$ line in each of the M unit gate blocks by a gate clock signal.

With this method, the flush operation is simultaneously performed for M lines, so that the time for the flush operation can be reduced to 1/M of the time for the progressive flush operation in the related art.

Meanwhile, in the multiple-channel-gate flush manner, multiple lines in a single unit gate block defined as in the multiple-channel flush manner are selected at the same time and the flush operation is performed for the selected lines at the same time. During operation in the multiple-gate flush manner, the number of flush cycles may be increased.

Specifically, as in the multiple-gate flush manner, the flush operation is performed in such a way that the gate stage of the image detector 23 is divided into M unit gate blocks each including N lines, a scan start pulse signal (Gate STV) is applied several times to each of the unit gate blocks at a time interval set in each of the unit gate blocks. Then, the N lines in each of the unit gate blocks are sequentially selected according to the scan start pulse signal (Gate STV) to apply a drive signal to the selected lines in the respective unit gate blocks at the same time.

Referring to FIG. 14, it can be seen that a scan start pulse signal (Gate STV) is applied twice at a certain time interval to the respective unit gate blocks, and that a drive signal (Gate Out) is simultaneously applied to the $1^{st}$ line and $101^{st}$ line of the respective unit gate blocks in response to the scan start pulse signal (Gate STV).

With this method, the drive signal may be applied to lines, which are simultaneously selected corresponding to the number of times of applying the scan start pulse signal, in the respective unit gate blocks, such that the number of times of performing the flush operation can be increased in the same period of operating time above the multiple-gate flush manner, thereby improving the rate of eliminating dark current accumulated in the pixels of the image detector 23.

In this way, the controller 27 shortens the time for the flush operation by performing the multiple-gate or multiple-channel-gate type flush operation, thereby minimizing loss of X-rays in an interface condition wherein X-rays are irradiated in a non-synchronous manner.

Then, the controller 27 checks whether the trigger signal informing of X-ray radiation is received (S200). If the trigger signal is received, the controller 27 checks whether the flush operation is being carried out through application of a drive signal to pixels in a line selected by the gate driver 24 (S300). In other words, the controller 27 checks whether the drive signal applied to the selected line is in an active state.

The trigger signal received by the controller 27 may be the exposure request signal (exp_req) sent from the X-ray generator 10 or the automatic exposure request signal (auto_exp_req) sent from the automatic exposure request signal generator 30, as described above.

If it is determined that the flush operation is being carried out by application of the drive signal to the pixels in the selected line, the controller 27 determines whether the flush operation is finished with respect to the selected line (S400).

Then, if it is determined that the flush operation is finished with respect to the selected line, the controller 27 completes preparation for exposure operation and then performs exposure operation (S500).

That is, when the flush operation is being carried out by application of the drive signal to the pixels in the selected line, the controller 27 completes preparation for exposure after completion of the flush operation with respect to the selected line, instead of immediately finishing application of the drive signal and preparation for exposure.

Referring to FIG. 14, upon receiving the automatic exposure request signal (auto_exp_req), the controller 27 may perform an exposure operation after completion of a current flush operation with respect to the $180^{th}$ line, instead of immediately performing the exposure operation.

As such, the exposure operation is performed after completion of the flush operation for a certain line, thereby preventing quality deterioration in each line and providing high quality image data.

If the flush operation is not carried out even after receiving the trigger signal, the controller 27 immediately completes preparation for exposure and performs an exposure operation (S500).

Although FIGS. 13 and 14 illustrate that the automatic exposure request signal (auto_exp_req) is received as the trigger signal from the automatic exposure request signal generator 30, the method according to the present invention may also be applied to the case in which an exposure request signal (exp_req) is received from a passive line trigger type X-ray generator 10.

Although some embodiments have been provided to illustrate the present invention, it should be understood that these embodiments are given by way of illustration only, and that various modifications, variations, and alterations can be made without departing from the spirit and scope of the present invention. The scope of the present invention should be limited only by the accompanying claims and equivalents thereof.

What is claimed is:

1. An X-ray imaging apparatus comprising:
   a scintillator panel which absorbs X-rays radiated from an X-ray generator and converts the X-rays into visible light;
   an image detector including a plurality of pixels arranged in a matrix array and charging the plurality of pixels with electric charges proportional to intensity of the visible light converted by the scintillator panel;
   a gate driver which selects a line in the image detector and applies a drive signal to pixels in the selected line;

an automatic exposure request signal generator which generates an automatic exposure request signal as a trigger signal informing of X-ray radiation through detection of X-rays radiated from the X-ray generator; and a controller which controls a time point of performing an exposure operation depending on a state of the drive signal applied to the pixels of the selected line in response to the automatic exposure request signal.

2. The X-ray imaging apparatus according to claim 1, wherein the controller completes preparation for the exposure operation after application of the drive signal is completed, when the drive signal applied to the pixels of the selected line is in an active state at a time point of receiving the automatic exposure request signal.

3. The X-ray imaging apparatus according to claim 1, wherein the automatic exposure request signal generator comprises:

a light converter which converts X-rays radiated from the X-ray generator into visible light;

a light detector which detects the visible light converted by the light converter and converts the visible light into an electric signal;

an amplifier which amplifies the electric signal converted by the light detector; and a trigger conversion circuit which converts the electric signal amplified by the amplifier into a digital signal to generate the automatic exposure request signal.

4. The X-ray imaging apparatus according to claim 3, wherein the light converter is a scintillator.

5. The X-ray imaging apparatus according to claim 1, wherein the automatic exposure request signal generator comprises:

a light detector which detects the visible light converted by the scintillator panel and converts the visible light into an electric signal;

an amplifier which amplifies the electric signal converted by the light detector; and a trigger conversion circuit which converts the electric signal amplified by the amplifier into a digital signal to generate the automatic exposure request signal.

6. The X-ray imaging apparatus according to claim 1, wherein the automatic exposure request signal generator comprises:

an X-ray detector which detects X-rays radiated from the X-ray generator and converts the X-rays into an electric signal;

an amplifier which amplifies the electric signal converted by the X-ray detector; and a trigger conversion circuit which converts the electric signal amplified by the amplifier into a digital signal to generate the automatic exposure request signal.

7. The X-ray imaging apparatus according to claim 1, wherein the automatic exposure request signal generator is placed on each of lower surfaces of the scintillator panel and the image detector with respect to a direction of radiated X-rays.

8. The X-ray imaging apparatus according to claim 1, wherein the automatic exposure request signal generator is placed at a location corresponding to a center or a corner of the image detector.

9. The X-ray imaging apparatus according to claim 1, further comprising: a read-out unit reading a value of charges in the pixels of the selected line.

* * * * *